(12) United States Patent
Lidahl et al.

(10) Patent No.: US 6,508,383 B2
(45) Date of Patent: Jan. 21, 2003

(54) DOOR SANITATION SYSTEM

(76) Inventors: Tom R. Lidahl, 214 Broadmore St., Plentywood, MT (US) 59254; Mary J. Lidahl, 214 Broadmore St., Plentywood, MT (US) 59254

( * ) Notice: Subject to any disclaimer, the term of this patent is extended or adjusted under 35 U.S.C. 154(b) by 49 days.

(21) Appl. No.: 09/801,426

(22) Filed: Mar. 7, 2001

(65) Prior Publication Data

US 2002/0127139 A1 Sep. 12, 2002

(51) Int. Cl.[7] .................................................. A47F 1/00
(52) U.S. Cl. ........................................ 221/97; 221/282
(58) Field of Search ............................. 221/45, 46, 49, 221/97, 185, 282, 286, 283; 206/449, 812, 494

(56) References Cited

U.S. PATENT DOCUMENTS

| | | |
|---|---|---|
| 3,819,043 A | 6/1974 | Harrison |
| 4,106,616 A | 8/1978 | Boone |
| 4,535,912 A | 8/1985 | Bonk |
| 4,735,317 A | 4/1988 | Sussman et al. |
| 4,873,728 A | 10/1989 | Bono |
| 4,998,984 A * | 3/1991 | McClendon ................ 206/205 |
| 5,647,506 A | 7/1997 | Julius |
| 5,753,246 A | 5/1998 | Peters |
| 5,938,069 A | 8/1999 | Macchia |
| 6,083,994 A * | 7/2000 | McCue ....................... 514/709 |
| 6,143,710 A * | 11/2000 | Lu et al. ..................... 510/384 |

* cited by examiner

Primary Examiner—Kenneth W. Noland
(74) Attorney, Agent, or Firm—Michael S. Neustel

(57) ABSTRACT

A door sanitation system for reducing the transmission of potentially harmful organisms, bacteria and viruses through physical contact with a door. The door sanitation system includes a base, a dispenser attached to the base for receiving a supply of towels, and a trash receptacle attached to the base. The towels within the dispenser are preferably saturated with a disinfecting solution. When preparing to leave a room through a door such as a restroom, the user removes at least one towel from the dispenser and positions the towel within the interior portion of their hand. The user then engages a portion of the door with their hand having the towel positioned in between thereof. As the towel engages the portion of the door such as a door handle, the disinfecting solution disinfects the surface of organisms, bacteria, and viruses. After the door is opened, the user then deposits the towel within the trash receptacle.

18 Claims, 6 Drawing Sheets

DOOR SANITATION SYSTEM

BACKGROUND OF THE INVENTION

1. Field of the Invention

The present invention relates generally to sanitation systems and more specifically it relates to a door sanitation system for reducing the transmission of potentially harmful organisms and viruses through physical contact with a door.

Harmful organisms, including bacteria, are widely diffused in nature, and multiply with rapidity, both by fission and by spores. Certain species of bacteria are the cause of certain infectious diseases. Viruses are simple submicroscopic parasites of plants, animals, and bacteria that often cause disease and that consist essentially of a core of IRNA or DNA surrounded by a protein coat. Since viruses are typically unable to replicate without a host cell, viruses are typically not considered living organisms.

Humans carry and transmit harmful organisms, bacteria and viruses everyday. A common type of transmission occurs when an infected individual directly touches another which enters the other person's body thereby infecting them also through various well-established means.

Another type of transmission occurs when an infected individual touches a location upon a door, such as a doorknob, door handle, push plate or other structure upon the door during the opening or closing of the door. Often times organisms, bacteria and viruses are left upon the exterior surface of the portion of the door touched. Organisms, bacteria and viruses can sometimes survive for hours after being positioned upon an object such as a door handle. When another individual physically touches the portion of the door containing the bacteria and/or virus, they have a high risk of becoming infected with the bacteria and/or virus. A common location for contamination to occur with the usage of doors is within a public restroom where individuals often times do not cleanse their hands prior to leaving. Various diseases such as but not limited to *escherichia coli* (a.k.a. *e. coli*), the common cold, staphylococcus, streptococcus, shigellosis and others are transmitted through physical contact with doors within public restrooms and doors in other locations of a building. Hence, there is a need for a sanitation system that not only protects an uninfected individual from being infected with a disease but that also cleanses areas upon a door that are commonly touched during usage.

2. Description of the Prior Art

Sanitation devices and solutions have been in use for years. An example of a common sanitation device a sanitary napkin containing a disinfectant for disinfecting surfaces. Disinfecting cleaning solutions have also been utilized for years and are common with the art.

The main problem with conventional cleaning devices and solutions is that they typically require a janitor or other designated individual to clean the surfaces at designated intervals which leaves time for inadvertent infections of a disease to occur between two individuals between cleanings. Another problem is that conventional sanitation devices and solutions are not conveniently positioned for an individual to utilize in reducing their risk of contamination.

Examples of patented sanitation devices and systems which are illustrative of such prior art include U.S. Pat. No. 5,647,506 to Julius; U.S. Pat. No. 3,819,043 to Harrison; U.S. Pat. No. 4,535,912 to Bonk; U.S. Pat. No. 5,753,246 to Peters; U.S. Pat. No. 4,106,616 to Boone; U.S. Pat. No. 4,735,317 to Sussman et al; U.S. Pat. No. 5,938,069 to Macchia; U.S. Pat. No. 4,873,728 to Bono; U.S. Pat. No. 4,998,984 to McClendon.

While these devices may be suitable for the particular purpose to which they address, they are not as suitable for reducing the transmission of potentially harmful organisms and viruses through physical contact with a door. Conventional sanitation systems and devices are not designed to be utilized throughout the day during normal usage of doors.

In these respects, the door sanitation system according to the present invention substantially departs from the conventional concepts and designs of the prior art, and in so doing provides an apparatus primarily developed for the purpose of reducing the transmission of potentially harmful organisms and viruses through physical contact with a door.

SUMMARY OF THE INVENTION

In view of the foregoing disadvantages inherent in the known types of sanitation devices now present in the prior art, the present invention provides a new door sanitation system construction wherein the same can be utilized for reducing the transmission of potentially harmful organisms and viruses through physical contact with a door.

The general purpose of the present invention, which will be described subsequently in greater detail, is to provide a new door sanitation system that has many of the advantages of the sanitation devices mentioned heretofore and many novel features that result in a new door sanitation system which is not anticipated, rendered obvious, suggested, or even implied by any of the prior art sanitation devices, either alone or in any combination thereof.

To attain this, the present invention generally comprises a base, a dispenser attached to the base for receiving a supply of towels, towelettes or wipes, and a trash receptacle attached to the base. The towels within the dispenser are preferably saturated with a disinfecting solution. When preparing to leave a room through a door such as a restroom, the user removes at least one towel from the dispenser and positions the towel within the interior portion of their hand. The user then engages a portion of the door with their hand having the towel positioned in between thereof. As the towel engages the portion of the door such as a door handle, the disinfecting solution disinfects the surface of organisms, bacteria, and viruses. After the door is opened, the user then deposits the towel within the trash receptacle.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction to the placement position or position on or near the door, and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a door sanitation system that will overcome the shortcomings of the prior art devices.

A second object is to provide a door sanitation system for reducing the transmission of potentially harmful organisms and viruses through physical contact with a door.

Another object is to provide a door sanitation system that prevents an infected individual from transmitting a disease to a surface upon a door.

An additional object is to provide a door sanitation system that cleans and disinfects a surface upon a door during the normal usage of the door.

A further object is to provide a door sanitation system that prevents the passing of a disease located upon a surface of a door to an individual coming in contact with the door.

Another object is to provide a door sanitation system that enables individuals to exit public restrooms without directly engaging doorknobs, door handles or push plates upon a door.

A further object is to provide a door sanitation system that reduces the spread of harmful organisms, bacteria and viruses to employees of a business that are in contact with food products such as in restaurants.

Another object is to provide a door sanitation system that simultaneously cleans and disinfects a user's hand(s) while opening/closing a door.

A further object is to provide a door sanitation system that enhances a business' public relations with consumers regarding cleanliness and disease control.

Another object is to provide a door sanitation system that is strategically placed upon or adjacent to a door to facilitate usage of disinfecting towels for opening and closing the door.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Figure 1:
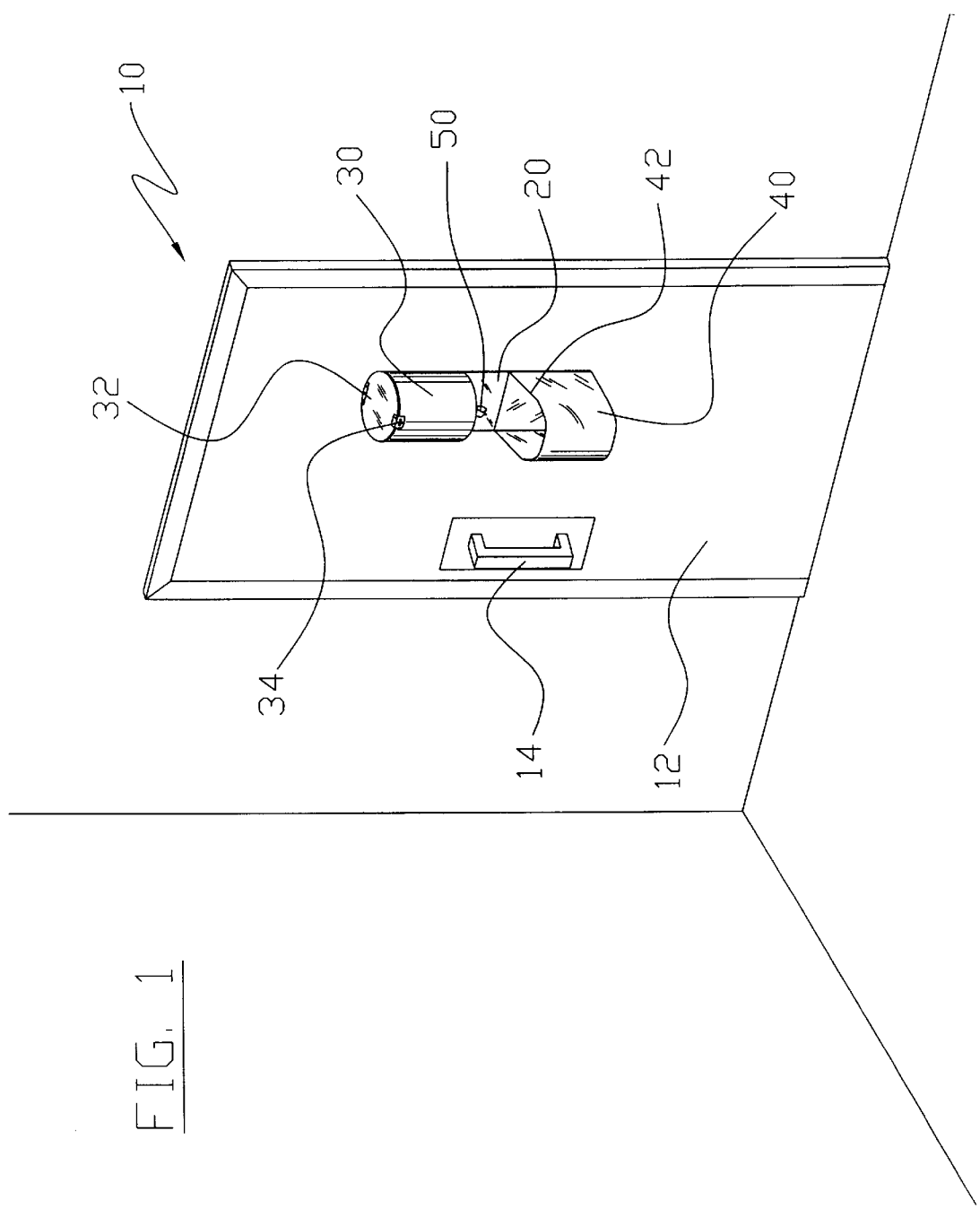
FIG. 1 is an upper perspective view of the present invention attached to a door.
Figure 2:
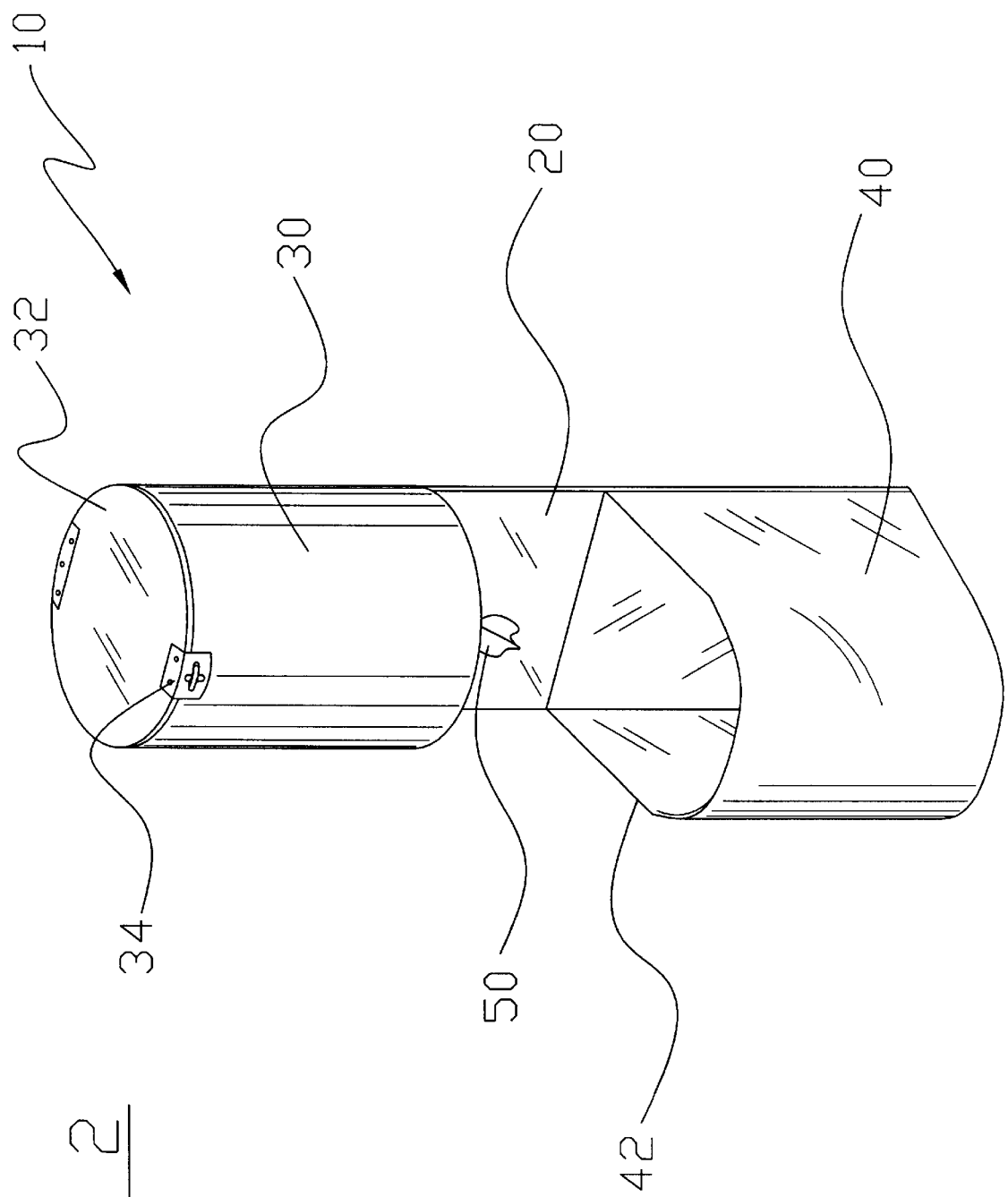
FIG. 2 is an upper perspective view of the present invention.

Turning now descriptively to the drawings, in which similar reference characters denote similar elements throughout the several views, FIGS. 1 through 6 illustrate a door sanitation system 10, which comprises a base 20, a dispenser 30 attached to the base 20 for receiving a supply 52 of towels 50, and a trash receptacle 40 attached to the base 20. The towels 50 within the dispenser 30 are preferably saturated with a disinfecting solution. When preparing to leave a room through a door 12 such as a restroom, the user removes at least one towel 50 from the dispenser 30 and positions the towel 50 within the inner portion of their hand. The user then engages a portion of the door 12 with theih and having the towel 50 positioned in between thereof. As the towel 50 engages the portion of the door 12 such as a door 12 handle 14, the disinfecting solution disinfects the surface of organisms, bacteria, and viruses. After the door 12 is opened, the user then deposits the towel 50 within the trash receptacle 40.

As shown in FIGS. 1 through 4 of the drawings, the base 20 is preferably a flat structure however various other structures may be utilized. The base 20 is attached to a door 12 or adjacent to the door 12 to facilitate usage of the towels 50 within the dispenser 30 a s shown in FIG. 1 of the drawings.

The dispenser 30 is preferably attached to the upper portion of the base 20, however it can be appreciated that the dispenser 30 can be attached anywhere upon the base 20 or directly to a wall or door 12. The dispenser 30 preferably includes a pivotally attached cover 32 with a latch 34 that exposes an interior 36 for receiving a supply 52 of towels 50 to be dispensed through at least one dispensing nozzle 38. As can be appreciated, various other configurations may be utilized to construct the dispenser 30 that are commonly utilized in the art.

Figure 3:
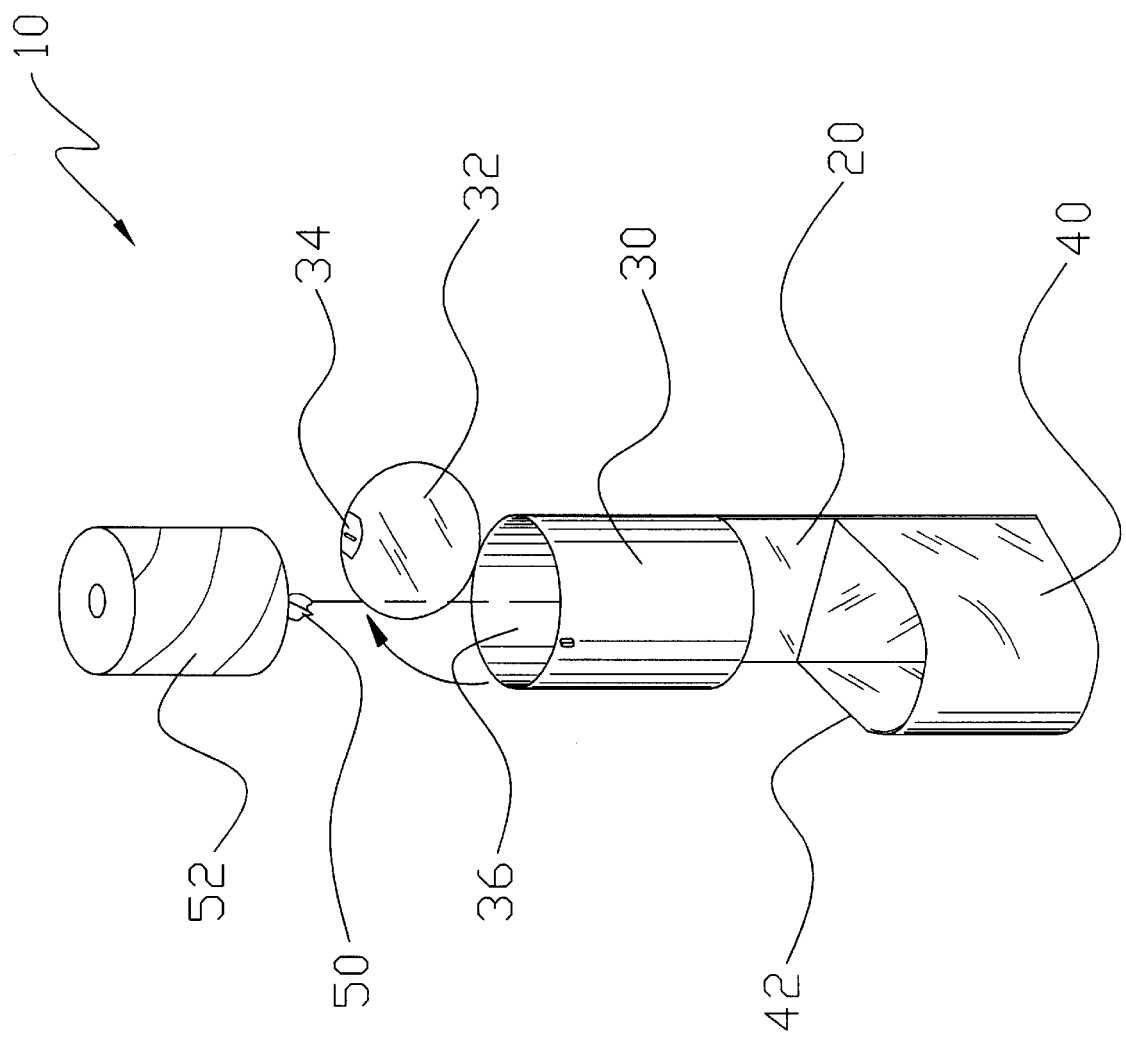
FIG. 3 is an exploded upper perspective view of the present invention.
Figure 4:
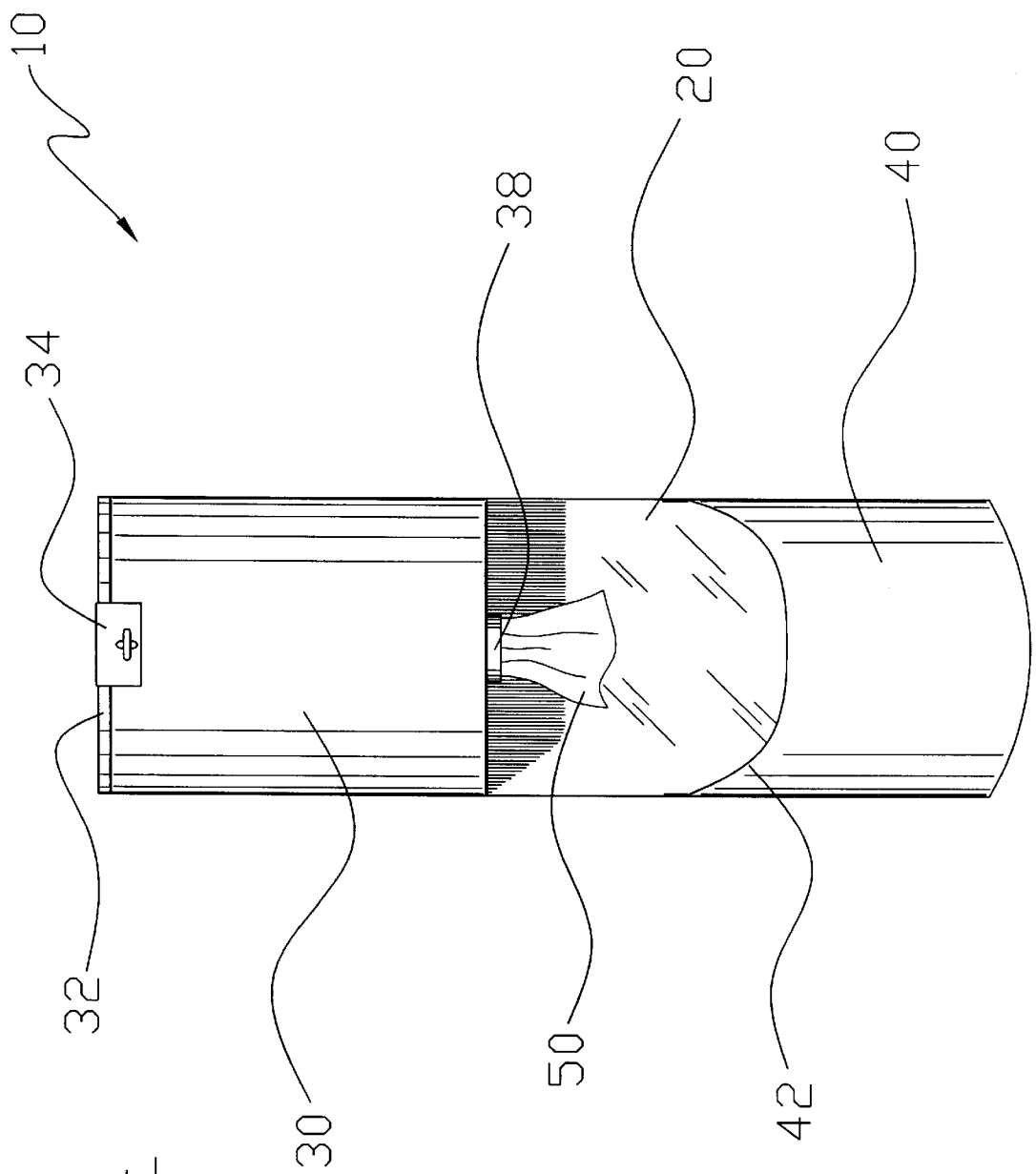
FIG. 4 is a front view of the present invention.

The dispenser 30 is preferably tubular in structure for receiving a volume of towels 50 such as but not limited to a spool 52 as shown in FIG. 3 of the drawings. Each towel 50 is preferably fully or partially saturated with a disinfecting solution. Disinfecting solutions are common in the sanitation industry and are hereby incorporated by reference. In addition, U.S. Pat. Nos. 4,998,984, 5,753,246 and 5,938,069 teach the usage of disinfecting solutions within a towel 50 structure which are hereby incorporated by reference for the purpose of disclosing possible disinfecting solutions to be incorporated into the towels 50. The towel 50 physical structure may also be comprised of any well-known towel 50 structure known in the art.

The trash receptacle 40 is preferably attached to the base 20 below the dispenser 30 as shown in FIGS. 1 through 4 of the drawings. The trash receptacle 40 has an upper opening 42 within that allows for the insertion of trash bags or the like to receive soiled and contaminated towels 50. It can be appreciated that the dispenser 30 and trash receptacle 40 could be separate structures not attached to a base 20.

Step #1: Removal of Towel

When an individual is prepared to leave a room such as a restroom, the individual approaches the door 12. Prior to engaging the door 12 or a handle 14 upon the door 12, the user grasps a towel 50 exposed through the dispensing nozzle 38 within the dispenser 30. If the user requires additional towels 50, they are then also removed from the dispenser 30. The user may want to at this time clean and disinfect their hands by manipulating the towel 50 between their hands thereby spreading the disinfecting solution within the towel 50 to their hands.

Step #2: Positioning of Towel

After withdrawing the desired number of towels 50, the user the must position the towel 50 within the interior 36 portion of their hand or hands depending upon how they intend to engage the door 12, doorknob, handle 14 or the like. The user preferably positions the towel 50 so that a majority of the inner portion of the hand is covered by the towel 50 as shown in FIG. 5 of the drawings.

Step #3: Engaging Portion of the Door

Figure 5:
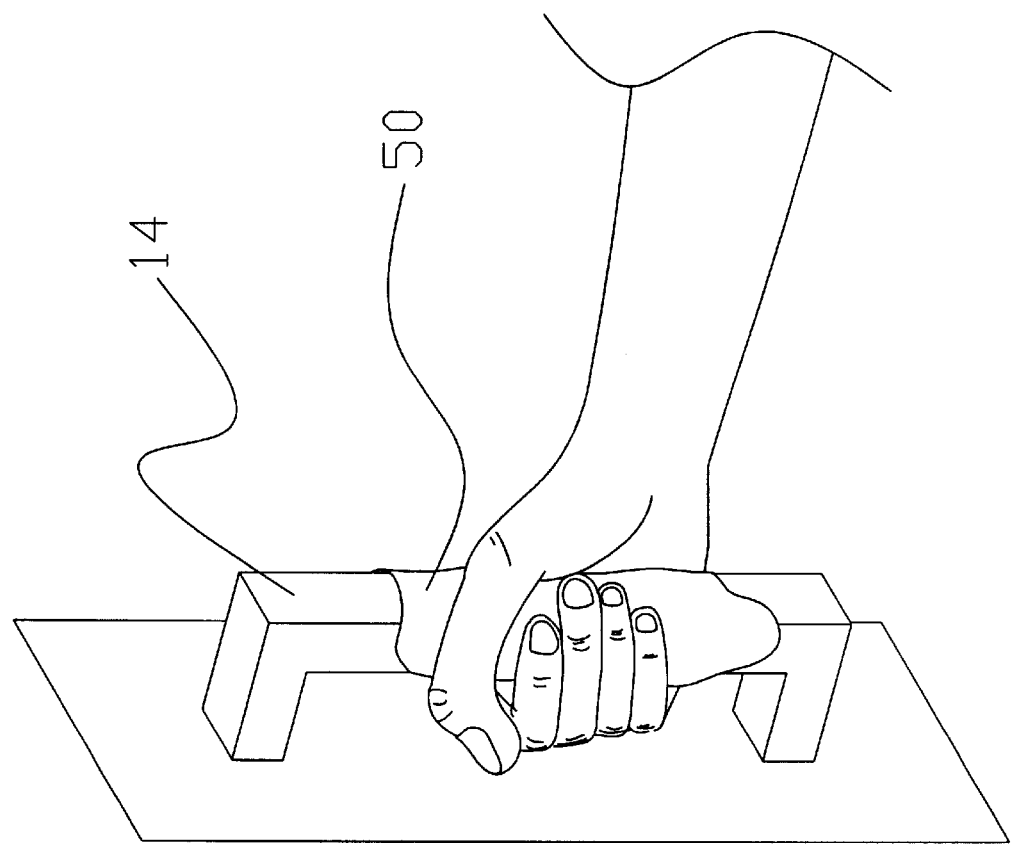
FIG. 5 is an upper perspective view of an individual grasping a door handle with a disinfectant towel positioned between the hand and the door handle.
Figure 6:
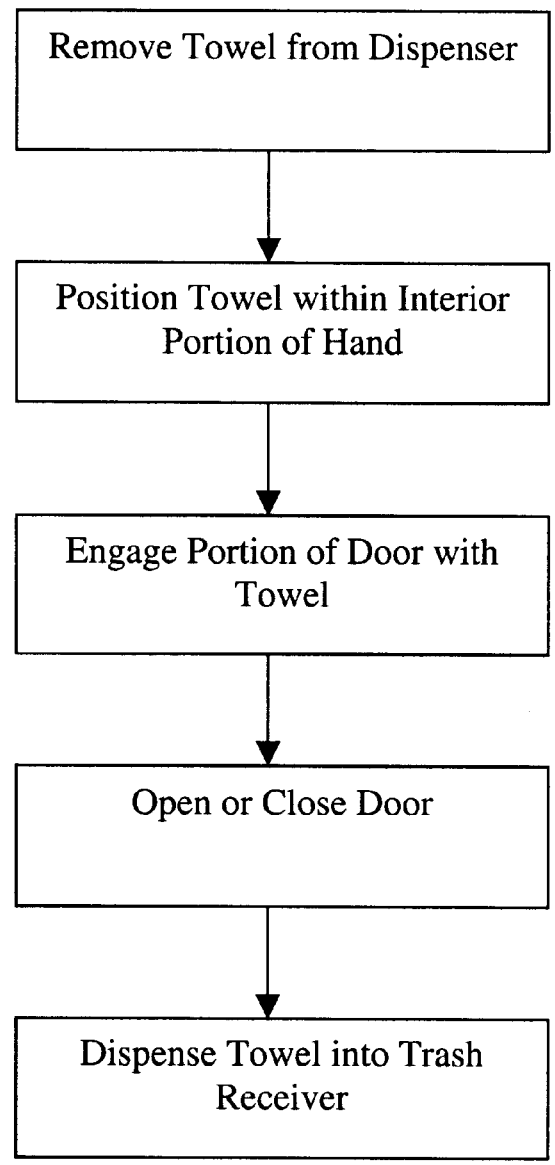
FIG. 6 is a flow chart illustrating the operation of the present invention.

After the towel 50 is properly positioned within the user's hand, the user engages the door 12, doorknob, handle 14 or the like to facilitate the opening or closing of the door 12 as shown in FIG. 5 of the drawings. The towel 50 is positioned between the inner portion of the hand and the handle 14 of the door 12 to prevent the hand from becoming in direct contact with the handle 14 or the door 12. This prevents any organisms, bacteria or viruses upon the user's hands from being spread to the handle 14 of the door 12 and prevents any organisms, bacteria or viruses upon the handle 14 of the door 12 from being spread to the hand of the user. In addition, the disinfecting solution is applied directly to the handle 14 of the door 12 thereby disinfecting the door 12 for later users.

Step #4: Opening or Closing Door

After the desired portion of the door 12 is engaged with the towel 50, the user then opens or closes the door 12 without any portion of their body directly touching the door 12 or parts thereof. After the door 12 is opened or closed, the user then removes their hand along with the towel 50 from the handle 14 of the door 12 without directly touching the contaminated side of the towel 50.

Step #5: Depositing Contaminated Towel

After the user's hand and towel 50 have been fully removed from the door 12 and parts thereof, the user then deposits the contaminated towel 50 into the trash receptacle 40 without touching the contaminated side of the towel 50. Later users are able to engage the handle 14 or door 12 knob of the door 12 with or without a towel 50 but still with a reduced risk of contamination.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A method of sanitization for reducing the transmission of organisms, bacteria and viruses through physical contact with portions of a door, wherein a dispenser and trash receptacle are attached to said door, comprising:
   (a) removing at least one towel from said dispenser;
   (b) positioning said towel within an inner portion of a hand; and
   (c) engaging a portion of said door and manipulating said door.

2. The method of sanitization of claim 1, including the step of:
   (d) removing said towel from said portion of said door.

3. The method of sanitization of claim 2, including the step of:
   (e) depositing said towel into said trash receptacle.

4. The method of sanitization of claim 1, wherein said step (b) further includes wiping at least one hand with said towel for cleaning and disinfecting said at least one hand.

5. The method of sanitization of claim 4, including the step of:
   (d) removing said towel from said portion of said door.

6. The method of sanitization of claim 5, including the step of:
   (e) depositing said towel into said trash receptacle.

7. A method of sanitization for reducing the transmission of organisms, bacteria and viruses through physical contact with portions of a door, wherein a dispenser and trash receptacle are attached to said door, comprising:
   (a) removing at least one towel from said dispenser containing a disinfecting solution within;
   (b) positioning said towel within an inner portion of a hand; and
   (c) engaging a portion of said door and manipulating said door.

8. The method of sanitization of claim 7, including the step of:
   (d) removing said towel from said portion of said door.

9. The method of sanitization of claim 8, including the step of:
   (e) depositing said towel into a trash receptacle.

10. The method of sanitization of claim 7, wherein said step (b) further includes wiping at least one hand with said towel for cleaning and disinfecting said at least one hand.

11. The method of sanitization of claim 10, including the step of:
    (d) removing said towel from said portion of said door.

12. The method of sanitization of claim 11, including the step of:
    (e) depositing said towel into a trash receptacle.

13. A method of sanitization for reducing the transmission of organisms, bacteria and viruses through physical contact with portions of a door, comprising:
    (a) securing a dispenser and a trash receptacle to said door;
    (b) removing at least one towel from said dispenser containing a disinfecting solution within;
    (c) positioning said towel within an inner portion of a hand; and
    (d) engaging a portion of said door and manipulating said door.

14. The method of sanitization of claim 13, including the step of:
    (d) removing said towel from said portion of said door.

15. The method of sanitization of claim 14, including the step of:
    (e) depositing said towel into a trash receptacle.

16. The method of sanitization of claim 13, wherein said step (b) further includes wiping at least one hand with said towel for cleaning and disinfecting said at least one hand.

17. The method of sanitization of claim 16, including the step of:
    (d) removing said towel from said portion of said door.

18. The method of sanitization of claim 17, including the step of:
    (e) depositing said towel into a trash receptacle.

* * * * *